(12) United States Patent
Dorel

(10) Patent No.: US 9,488,473 B2
(45) Date of Patent: Nov. 8, 2016

(54) METHOD AND DEVICE FOR MEASURING THE FLATNESS OF A METAL PRODUCT

(71) Applicant: PRIMETALS TECHNOLOGIES AUSTRIA GMBH, Linz (AT)

(72) Inventor: Laurent Dorel, Montbrison (FR)

(73) Assignee: Primetals Technologies Austria GmbH, Linz (AT)

( * ) Notice: Subject to any disclaimer, the term of this patent is extended or adjusted under 35 U.S.C. 154(b) by 85 days.

(21) Appl. No.: 14/390,821

(22) PCT Filed: Apr. 3, 2013

(86) PCT No.: PCT/EP2013/057035
§ 371 (c)(1),
(2) Date: Oct. 6, 2014

(87) PCT Pub. No.: WO2013/150075
PCT Pub. Date: Oct. 10, 2013

(65) Prior Publication Data
US 2015/0116727 A1 Apr. 30, 2015

(30) Foreign Application Priority Data

Apr. 4, 2012 (EP) .................................. 12290121

(51) Int. Cl.
*G01N 21/86* (2006.01)
*G01N 21/892* (2006.01)
(Continued)

(52) U.S. Cl.
CPC ......... *G01B 11/303* (2013.01); *G01B 11/2522* (2013.01); *G01B 11/306* (2013.01);
(Continued)

(58) Field of Classification Search
CPC ............. G01B 11/303; G01N 21/892; G01N 21/8914; G01N 21/86; G01N 2021/8918; G01N 2201/06113; G01N 2201/02
USPC .......... 356/429–431, 238.1–238.5, 318, 317, 356/73.1, 237.1, 71; 382/141
See application file for complete search history.

(56) References Cited

U.S. PATENT DOCUMENTS 4,759,072 A * 7/1988 Yamane .................. G01N 25/72
250/330
5,465,214 A * 11/1995 Jeuniaux ............... G01B 11/306
700/117
(Continued)

FOREIGN PATENT DOCUMENTS

CN 1182211 A 5/1998
CN 1982869 A 6/2007
(Continued)

OTHER PUBLICATIONS

Badger, J.C. et al: "Automated Surface Inspection System" Aise Steel Technology, Aise, Pittsburg, PA, US, vol. 73, No. 3, Mar. 1, 1996, pp. 48-51, XP000587196, ISSN: 0021-1559 the whole document.

*Primary Examiner* — Sang Nguyen
(74) *Attorney, Agent, or Firm* — Laurence A. Greenberg; Werner H. Stemer; Ralph E. Locher

(57) ABSTRACT

A method measures the flatness of a metal product and an associated device. The method applies to a metal product, in the form of either a strip or a plate from a metallurgical processing line. The product to be measured being, by default, free of external traction. The method contains the following steps: a) illuminating a portion of a face of the product under uniform intensity; b) capturing an image of a light line of the illuminated portion; c) relatively moving the illuminated portion and the light line in a defined direction in relation to the product; d) repeating steps a), b), c); and e) collecting the images of lines in a two-dimensional distribution of intensities and selecting a strand direction of the product in which, if at least one wave of intensities is detected, a local amplitude variation of the wave delivers a local strand flatness defect value.

20 Claims, 3 Drawing Sheets

(51) Int. Cl.
*G01B 11/30* (2006.01)
*G01B 11/25* (2006.01)
*G01N 21/89* (2006.01)

(52) U.S. Cl.
CPC ......... *G01N 21/86* (2013.01); *G01N 21/8901* (2013.01); *G01N 21/892* (2013.01); *G01N 21/8914* (2013.01); *G01N 2021/8918* (2013.01); *G01N 2201/02* (2013.01); *G01N 2201/06113* (2013.01)

(56) References Cited

U.S. PATENT DOCUMENTS

| | | | |
|---|---|---|---|
| 5,661,552 A * | 8/1997 | Nishigai | G07D 7/10 250/556 |
| 5,894,345 A | 4/1999 | Takamoto et al. | |
| 6,067,162 A | 5/2000 | Hagen et al. | |
| 7,503,680 B2 | 3/2009 | Desvaud | |
| 8,164,750 B2 * | 4/2012 | Shimazu | B07C 5/3425 209/580 |
| 8,334,986 B2 * | 12/2012 | Moll | G01B 11/0625 356/601 |
| 2002/0039187 A1 * | 4/2002 | Keranen | G01B 11/2522 356/604 |
| 2006/0002605 A1 * | 1/2006 | Chang | G01N 21/952 382/141 |
| 2006/0274930 A1 | 12/2006 | Laurent et al. | |
| 2007/0115473 A1 * | 5/2007 | Legoupil | G01N 21/8901 356/430 |
| 2007/0171661 A1 | 7/2007 | Desvaud | |
| 2007/0188739 A1 * | 8/2007 | Aoshima | G01M 11/37 356/73.1 |
| 2008/0018892 A1 * | 1/2008 | Haugholt | G01N 21/49 356/318 |
| 2008/0302707 A1 * | 12/2008 | Bourely | B07C 5/34 209/577 |
| 2009/0002707 A1 * | 1/2009 | Berger | G01N 21/8915 356/430 |

FOREIGN PATENT DOCUMENTS

| | | | | |
|---|---|---|---|---|
| CN | 101226158 A | 7/2008 | | |
| CN | 102223959 A | 10/2011 | | |
| DE | 3345198 A1 * | 6/1985 | | G01B 7/06 |
| DE | 102006051538 A1 | 4/2008 | | |
| EP | 1890134 A1 | 2/2008 | | |
| FR | 2595815 A1 | 9/1987 | | |
| FR | 2895084 A1 | 6/2007 | | |
| WO | 9518952 A1 | 7/1995 | | |
| WO | 2004063664 A1 | 7/2004 | | |

* cited by examiner

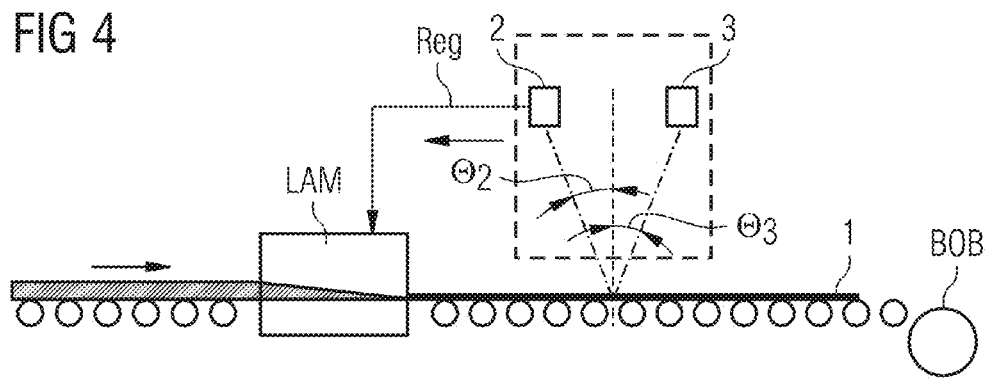
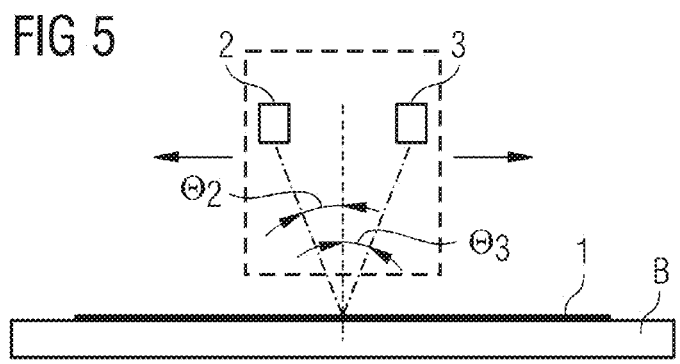
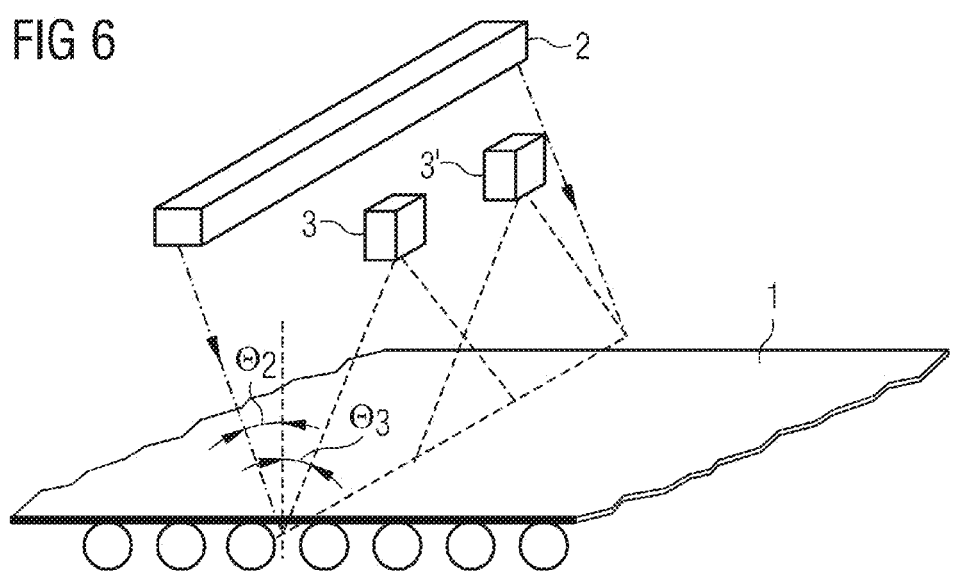

METHOD AND DEVICE FOR MEASURING THE FLATNESS OF A METAL PRODUCT

A method and device for measuring the flatness of a metal product

BACKGROUND OF THE INVENTION

Field of the Invention

The present invention relates to a method for measuring the flatness of a metal product such as a strip or a plate and an associated device according to the preambles of claims 1 and 12.

There is a device for measuring the flatness of a metal strip in a metallurgical processing line, in particular intended to be rolled. An example originating from the present applicant consists of a roll (known as a Planicim™ roll or other roll commonly called a "Shapemeter roll") measuring variations in forces applied to a set of points in the cross-section of a strip traveling over said measuring roll. In this way, said forces can be compared to longitudinal tractions applied to the strip, but also more schematically to strands (per transverse measuring point) of a strip positioned between the strip edges. This measuring roll has exceptional measuring quality for strips traveling under traction, since they are mainly subjected to tractions when measuring flatness. This device is however more limited when there is a need to measure not a strip (with a maximum thickness of ~10 mm) but a thicker plate.

In this respect, another system operates to measure the flatness of very thick plates (for example from 5 mm to more than 150 mm). This laser measuring device also represents considerable cost and, like the other preceding devices, it may thus be found to be financially senseless even to reach its measuring limits for strip flatness measurements when said strip is in a phase not associated with external (longitudinal) tractions. In fact, it is found that, with no or at least very little strip traction, strip strands (from the center to the edges) present highly specific artifacts making it impossible to measure a minute residual traction value and thus make a good assessment of flatness as with the principle of the measuring roll for a strip under traction.

Another known method for measuring flatness consists in measuring an amplitude vibration of a flat metal product under longitudinal traction resulting from the vibration excitation of said product generated by alternating pulse suction on the product traveling across a pneumatic unit (see applicant's publication EP2344286). Similarly, this method requires the presence of external traction on the product to hold it on each side of the excited portion. This external traction may thus induce uncertainty in the measurement of the real intrinsic traction of the product which the present invention is attempting to measure.

Finally, an alternative for measuring the flatness of a metal product consists, according to JP20110099821, in projecting a light matrix onto a portion of the surface of the metal product consisting of binary coded optical information (of the fringe or checkerboard type, "in black and white") and a display system (CCD camera) making an acquisition of a two-dimensional image of the matrix projected, which, in the event of non-flatness of the product in the form of a local wave, makes it possible to record phase shifts between the fringes or checkerboards projected and those of an ideal reference network (of a flat surface). On the basis of these measurements of phase variations, the flatness of the illuminated/displayed surface zone of the product is calculated.

In the case of a traveling product (for example a strip traveling at more than 150 m/min), it would, however, be necessary, for such a measurement system, to stop the traveling strip in order to perform a measurement, otherwise the phase measurements are no longer relevant. Even though this method seems not to introduce external traction on the product, this aspect of immobilization of the product is very awkward for continuously running or alternating/reversible installations, requiring at least constant (and if possible maximum) movement of the product. In the case of a metal product which is not very reflective or even being hot-rolled (at least 400° C.), it is found to be more difficult to obtain an adequate light signal-to-noise ratio on a large surface of the product illuminated by the matrix projected.

BRIEF SUMMARY OF THE INVENTION

An object of the present invention is to propose a method for measuring the flatness of a metal product not by default subjected to any (external) traction at the point of measurement on the processing line where it is located, but able by extension, however, to undergo (external) traction. This therefore involves proposing a more universal system, simple and dynamically more efficient than those set out above.

Proposing an associated device making it possible to implement this method is a second object of the invention while guaranteeing, among other things, its simplicity, its reduced cost and its high measurement dynamics.

The invention thus proposes a method for measuring the flatness of a metal product and an associated device to implement it.

Said method for measuring the flatness of a metal product in the form of either a strip or a plate from a metallurgical processing line, said product to be measured being, by default, free of external traction, thus comprises the following steps:
a) illuminating a (slender) portion of at least one face of said product under uniform intensity
b) capturing an image of a light line of the illuminated portion
c) relatively moving the illuminated portion and the light line in a defined direction in relation to the product
d) repeating steps a), b), c)
e) collecting the images of lines in a two-dimensional distribution of intensities and selecting a strand direction of the product in which, if at least one wave of intensities (the term "wave" means at least one intensity variation of the "hollow/bump" type detected locally on several successive intervals of the strand) is detected, a local amplitude variation of said wave delivers a local strand flatness defect value.

In fact, without any external traction action, and in the case when the product is, at its simplest, positioned on a conveyor belt or table, the product no longer presents intrinsic properties in terms of flatness which are presented as strands under different internal stresses and therefore under different lengths. Given that the strands are physically side by side, the result is that the longest strands form bumps and hollows visible on the surface (these bumps and hollows being able to run from about one cm to more than 30 cm in length for products such as a strip with dimensions of 2 m×1 km and 2 mm thick, for example). It appears that these effects which we have called here (local) waves or undulations are flatness measurement values and that, under a lighting plane which is oblique in relation to the metal surface of the product and doubly oblique in relation to the plane of display of the illuminated surface, they induce differences in light reflection in relation to an ideally flat metal surface. Thus, knowing that a light line capture has been performed and in the case of a bump or hollow cutting this line, reductions or (re-)increases in the light intensity of the line observed will be recorded. The condition for obtaining such a condition is that the line or at least the light strip projected cuts, and therefore is not parallel to, the light line whose image has been captured.

Finally, the direction of the strand is preferably selected along the length of the product, but it is quite possible to choose it to be more oblique or even transverse on the product so as to be able also to measure flatness defects more spread across the width of the metal strip/plate. This aspect of the invention of being able to choose the direction of the strands measured also makes it possible to make the measurement of non-flatness more dynamically suitable for evaluating a transverse tile-effect defect in the product, but also other more longitudinal non-flatness defects, the waves of which detected one after the other on a strand present variable lengths (or periods).

At its simplest in a metallurgical line or a test bench, the method according to the invention provides that the illuminated portion extends at least over the width of the product and the strand direction selected is along the length of the product. This aspect makes it possible simply to make the product travel opposite an illumination/display assembly (corresponding to steps a) and b) mentioned previously). Thus, a relative movement between the product and the assembly comprising the means of illumination and image capture is implemented either by travel of the product in the line, or by movement of said means for a product which is motionless in the line.

In practice, the illuminated portion of slender shape over the width of the product is generated by a light source such as, at its simplest, at least one laser source or a strip light comprising at least one light source placed opposite the product which is traveling relative to said source or the strip light. The illumination (strip light or point source) and display assembly is then arranged in an optical triangulation configuration opposite the product. In the case of triangulation by a single point laser source generating a laser line projected onto the surface of the product, the deformation of said line on a matrix camera for displaying the intensities of the projected line delivers a product height in relation to its plane of movement/travel. Said height delivered over a product strand thus makes possible a simple and rapid measurement of flatness (hollows/bumps) over said strand.

Subsequently, figures and sub-claims illustrate advantageous aspects of the method according to the invention and present embodiments of devices providing for the implementation of said method.

BRIEF DESCRIPTION OF THE SEVERAL VIEWS OF THE DRAWINGS

FIG. 4: Implementation of the method at the output from a hot-rolling mill FIG. 5: Implementation of the method on a test bench FIG. 6: Enhancement of the dynamics of the measuring method

DESCRIPTION OF THE INVENTION

Figure 1:
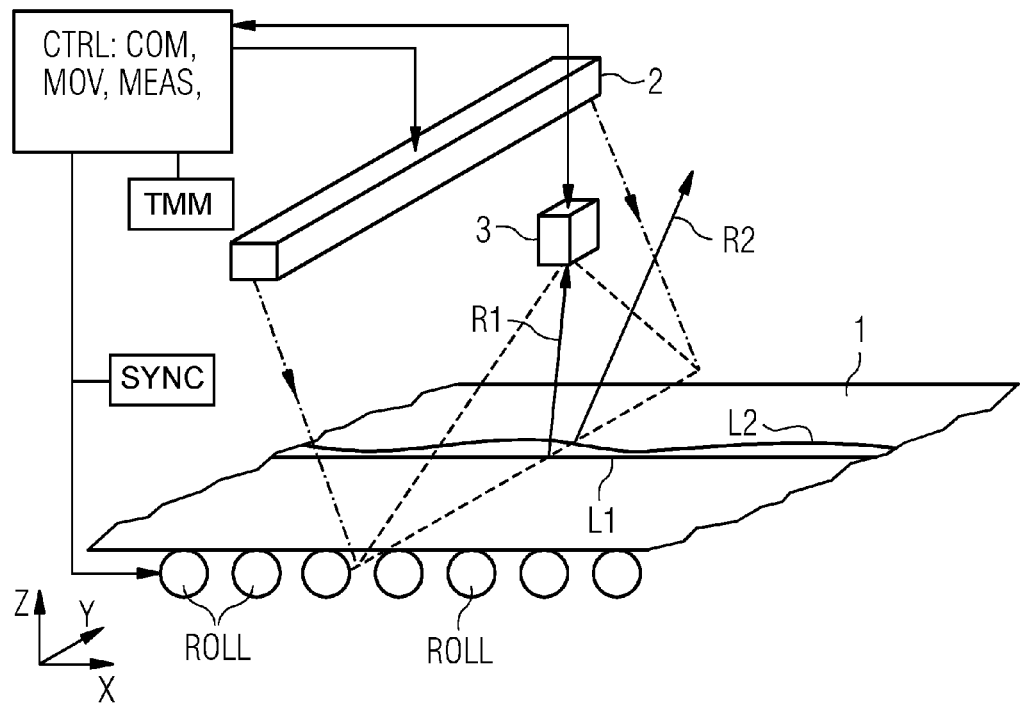
FIG. 1: Schematic device for implementing the method for measuring flatness according to the invention

FIG. 1 mainly presents a device for implementing the method for measuring the flatness of a metal product (1), in the form of either a strip or a plate from a metallurgical processing line, said product to be measured being, by default, free of external traction, comprising:

at least one strip light (2) positioned in the vicinity of a face of the product and illuminating a (at least linear) portion of that face at least one linear camera (3) to capture an image of said portion a means of transport (ROLL)—here conveyor rolls—along a direction (X) of movement of the product in the processing line providing for a relative movement of the strip light and camera assembly in relation to the product in said direction a control module (CTRL, COM, MOV, SYNC) for the strip light and the camera in order to activate and coordinate steps a), b), c), d) of the measuring method a unit (MEAS) for processing the data delivered by the camera receiving the images in order to collect them and deduce flatness values for the strands selected according to step e) of the measuring method In particular, the device comprises a synchronization unit (SYNC) between the control module and the means of transport. In FIG. 1, this means of transport may be a hot-rolling mill stand (or a cold- or hot-rolling heavy sheet leveler), a roll table, a conveyor belt or a coiling plant, said means of transport being driven so as to make the product/strip/plate (1) travel along its longitudinal direction X. In principle, the device provides that the means of transport is a means making the product travel in front of the assembly formed by the strip light and the camera or vice-versa, i.e. that the assembly formed by the strip light and the camera is translated in relation to a face of the product (which can then be motionless, for example on a flat support).

In order better to present the measurement of flatness in diagram form, two strands (L1, L2) have been selected quasi-adjacent and parallel along longitudinal direction X. It is assumed that the first strand (L1) has perfect flatness (thus the strand is rectilinear along direction X) and that the second (L2) strand has undulation indicating imperfect flatness (bump/hollow deviation in the plane X, Z), the product (1) here being mostly not under traction. However, the product could also subsidiarily be subjected to external traction not represented here in FIG. 1. This may be implemented by any means of line traction. In this case, the data processing unit (MEAS) is connected to an associated module for measuring the traction TMM applied to the product, acting in particular in addition to (measured) traction intrinsic to said product. Thus, although the associated measurement module only measures for example low non-flatness values, the method according to the invention can provide a measurement over a more extensive range of non-flatness values.

The method according to the invention according to FIG. 1 thus presents a detected wave of light intensities resulting from a variation in orientation of the hollow and bump type in each strand—here the second strand (L2)—inducing a variation in the amplitude of the intensities measured (by the linear camera 3), which can be compared to an evaluation of the length of each of the strands under its own intrinsic traction and having its own flatness value. In the case of the first strand (L1), a constant light reflection (R1) arrives at the linear camera (3) and the measured amplitude remains maximum along the strand, while the product (1) and the assembly formed by the strip light and the camera are in relative movement. This is not the case for the second strand (L2) for which, during relative movement, variations in light reflection (R2) are recorded by the data processing (MEAS, connected to the linear camera), knowing that the principal angle of reflected light varies and does not remain in the same position in relation to the angular field of the camera provided to receive direct reflections of the illumination on the product (angle of incidence close to the angle of reflection). From these light variations originating from angles of light reflection, waves of the bump/hollow type can then be measured and finally the length of each strand can be evaluated and converted into a flatness value.

The method according to the invention provides that the product can be subjected to external longitudinal traction forces. For this purpose, the direction of the strand measured can also be selected in the plane X, Y in order to measure waves revealing suspected non-flatnesses for a product (tile effect, for example, if taking the transverse direction as the direction of travel).

Experimentally, the method according to the invention provides for very effective measurement of the flatness of the product to be checked for variable processing line thicknesses, particularly between 0.1 mm and at least 150 mm. This is why it is particularly well suited for metal products including strips (thinner) and plates (thicker). In this respect, the more universal measurement method is thus applicable at the input and/or output of the rolling or leveling installation for products produced by both cold- and hot-rolling.

Figure 2:
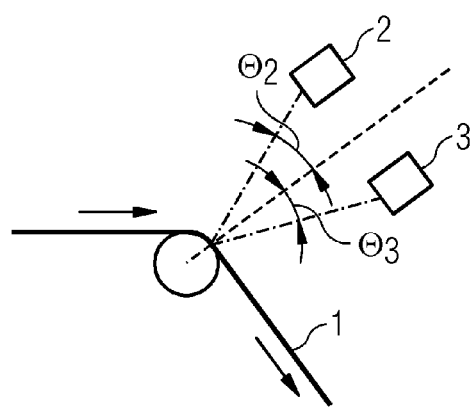
FIG. 2: Arrangement for measuring on a deflecting roll

FIG. 2 presents a measurement arrangement on a roll wherein the method according to the invention provides that the illumination (2) and image capture (3) are performed for a product cross-section, said cross-section being observed on a deflecting roll along one of its generating lines in contact with the product (1) moving above. The angle ($\theta_2$) formed by the illumination curtain (2) in relation to a median plane—in fine dotted lines—passing through the axis of rotation of the roll is the same as or close to the angle ($\theta_3$) formed by the plane of image capture (3) passing in relation to said median plane. Thanks to this configuration and assuming that the deflecting roll over which the product passes can also be a strip traction measuring roll (therefore a flatness measurer), the measurement method according to the invention performs the flatness measurement by raising the range of measurable flatness values initially measured by the measuring roll. This complementarity of measurements is a major advantage for example if it is found that there is a high degree of non-flatness (producing for example a partial detachment effect on the coiled strip on an angular sector of the external surface of the roll), in which case the roll for measuring flatness under traction does not deliver a relevant value for flatness/traction at this point. So it is the method according to the invention which easily detects flatness defects in the detachment zones.

Figure 3:
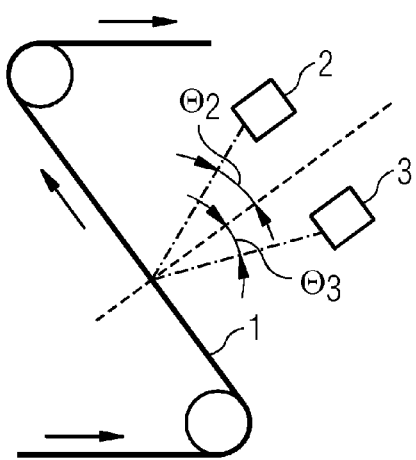
FIG. 3: Arrangement for measuring between deflecting rolls

FIG. 3 presents a measurement arrangement (2, 3, $\theta_2$, $\theta_3$) identical to that in FIG. 2 but positioned between deflecting rolls wherein the method according to the invention provides that the illumination (2) and image capture (3) are performed for a product cross-section (1), said cross-section being under tension between the two deflecting rolls, free of any support for one of its faces, in particular in the case where the product is a traveling metal strip. Naturally, depending on the metallurgical line configurations, the spatial orientation of the tangential plane formed upon deflection contact of the deflecting rolls may be anything. Under this configuration and assuming that the traveling strip is not subjected to excessive vibratory effects to disrupt the measurement, flatness measurement artifacts induced by roll bending/wear effects (as in FIG. 2) may be advantageously removed. It should be noted that the present method for measuring flatness delivers non-flatness values running from a cm to several tens of cm for products with dimensions of about 2 m×1 km. Vibrations may thus be tolerable below a cm (minimum flatness measurement value) if the strip tension is correctly adjusted.

Similarly to FIG. 1, FIGS. 4 and 5 present respectively an implementation of the method according to the invention at the output from a rolling mill and an implementation of the method on a test bench.

Thus, the method according to the invention provides that the illumination and image capture are performed for a product cross-section, said cross-section being located on a flat transverse zone, such as a succession of upper roll generating lines, known as a roll table, a conveyor belt (see succession of rolls under the product 1, FIG. 4) or a fixed support table (B) (see FIG. 5). The illumination and image capture are performed for a product cross-section, said cross-section being located at the input and/or output of a metallurgical processing section such as a rolling mill (LAM) or a leveler, the product respectively comprising mainly a cold-rolled or hot-rolled metal. This flatness measurement, for which no traction (by conveying during rolling when the head of the rolled strip has not yet been coiled by the output coiler or during leveling) or external traction (principally exerted by the output coiler) are quite possible, depending on the position of the product, is a major piece of information describing the freshly rolled or leveled product under appropriate initial flatness tolerances so that the product can undergo other operations downstream of metallurgical, mechanical/chemical or other processes in order to become a high quality end product. The method according to the invention operating without traction or otherwise is therefore highly suitable in such a case. Also, if a coiler (BOB) is positioned at the end of conveying output downstream of a rolling mill (LAM), the measuring method according to the invention can be executed on a part of a traveling product before being coiled on the coiler. Here the traction of the coiler must be taken into account in the process of flatness measurement.

Finally, FIG. 4 (as well as the other figures such as 1, 2, even if not represented) illustrate a potential advantageous use of the method according to the invention as input data (REG) for a rolling mill (LAM) or leveler operating regulator wherein the method measures the flatness of a product emerging from the rolling mill or leveler, then transmits control instructions to evaluate and, depending on the quality criteria imposed, correct the measured flatness of the product emerging from the rolling mill or leveler.

The method according to the invention and a device like that in the preceding FIGS. 1, 2, 3, 4 can also be easily implemented for measuring flatness involving reversible movement (right-left along direction X on FIG. 1 or 4) of the product during metallurgical processing. Here again, the measurement can be made in or outside a rolling mill or a leveler, without or with traction.

In FIG. 5, it should be noted that the product is positioned horizontally on a flat fixed support above which the assembly formed by the strip light (2) and the camera (3)—at respective opposed angles ($\theta_2$, $\theta_3$) of incidence in relation to the plane of the product—is moved longitudinally or transversely by a trolley circulating parallel to an inspected face of the motionless product.

In principle, the device presented in FIG. 1 is to allow automatic inspection of a moving strip, in particular as part for example of quality control for micro-defects (a few microns) arising from the manufacture of a steel strip capable of being coiled, and comprises a first arrangement for illumination over a zone with at least the width of the strip and a second arrangement for the acquisition of images of said zone. Such arrangements are for example well described by patent FR 05 5 13105 presenting, as an illumination arrangement, a strip light comprising a series of light diodes positioned across the width of the strip light and optics making it possible to generate a light curtain originating from high-power light-emitting diodes and passing across at least the width of the moving strip. The image acquisition arrangement comprises at least one camera (at least linear) the acquisition rate of which is sufficiently rapid in relation to the rate of travel of the strip in order to obtain sequences of portions of strips so as to reconstitute an image of the complete strip. The two arrangements present two main optical axes forming an angle known as triangulation and intersecting on the strip. Usually, diodes of various colors (or wavelengths) can be chosen to be installed in a strip light and the camera, usually a simple black-and-white camera (gray level) presents a means for filtering said color.

In the case of the present invention, the inspection device, even though analog, is not intended for measurement ranges below a mm, i.e. it does not deliver topographic values (in X, Y, Z) for surface defects (in X, Y, Z) in metal products, but measures variations in intensities and therefore in portions of lengths in increments of a few cm on strands mainly of great length (5 m or more). The method according to the invention is therefore a distinct measuring application for systems such as that in FR 05 13105. It follows that a person skilled in the art wishing to obtain such a system could, at little cost, implement two distinct measuring methods, namely not only to have it measure surface microdefects, but also more macroscopic traction and thus flatness defects. These two measuring methods could collaterally be implemented as a computer program in the control module CTRL and the data processing module MEAS according to FIG. 1, which would act as a support for the two micro-defect and flatness measurement algorithms.

FIG. 6 presents a dynamic enhancement of the measuring method according to the invention (such as for example described in FIGS. 1, 2, 3, 4, 5) in that several linear cameras (3, 3') are spread along a transversal of the light line to be observed (here a transversal of the product). This has several advantages, including:
  increase in the amplitude/intensity measurement dynamics, since the range measured by the camera is more limited and therefore more intensively illuminated/observed—this is noticeable in the case of a less reflective product such as hot-rolled or matt/dark products subjected to weaker light reflections from the illuminated zone
  better uniformity of the intensities at the cameras (since the strip light must illuminate uniformly over the portion, here transversal)—brings a considerable advantage at the rims/edges of the product since there is greater distribution of the light reflected and thus measurable.

Figure 7:
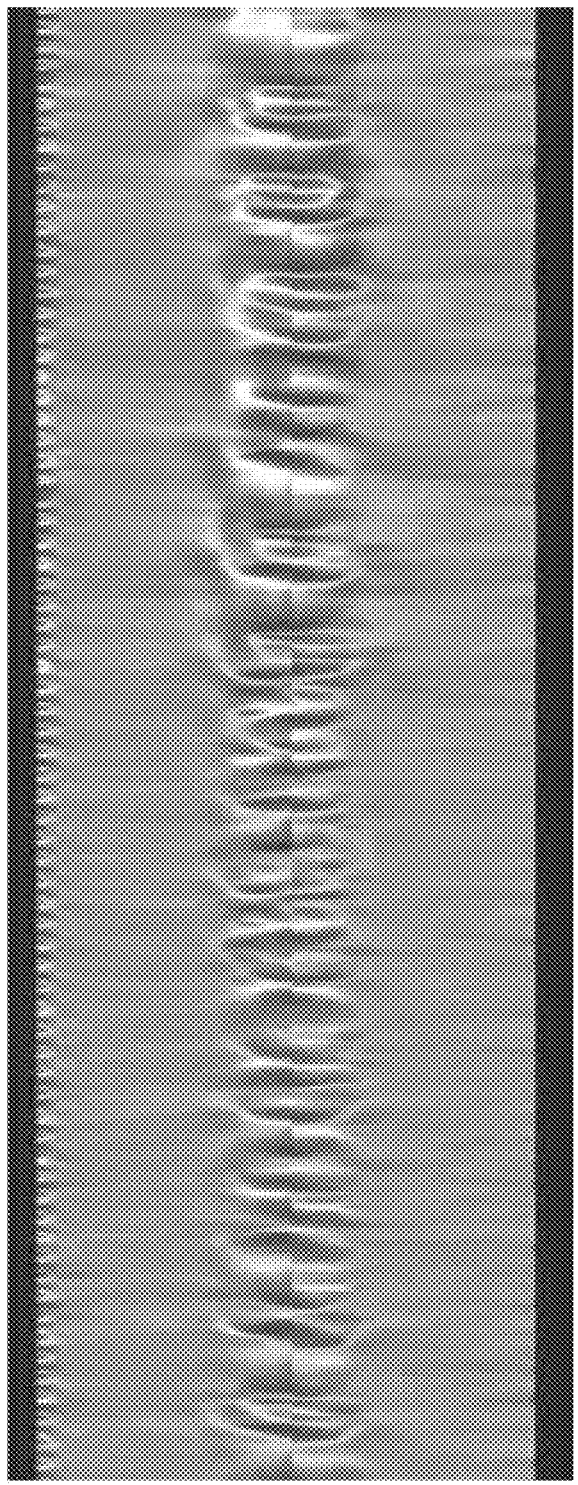
FIG. 7: Measurement of flatness of a metal strip under no traction

Finally, FIG. 7 presents an example of measurement of the flatness of a metal strip under no traction obtained using the method according to the invention according to FIG. 6. The metal strip measured has dimensions of 2 m×1 km and a thickness of 2 mm, the image represents a part of the strip measuring 2 m×50 m. Waves of the bump/hollow type of the order of a cm up to several tens of cm are clearly measured automatically and make it possible to observe the tractions or intrinsic flatness defects in the strip following single and rapid travel (no traction or at least almost negligible traction) of the strip on a conveyor belt. The device used for this measurement is a system adapted from that described by FR 05 13105, as described above and the costs associated with this adaptation are found to be very minimal in comparison with the acquisition of an existing flatness measurement system on the current market.

The invention claimed is:

1. A method for measuring a flatness of a metal product selected from the group consisting of strips and plates from a metallurgical processing line, which comprises the following steps:
  a) illuminating a portion of at least one face of the metal product under uniform intensity;
  b) capturing an image of a light line of an illuminated portion of the metal product;
  c) relatively moving the illuminated portion and the light line in a defined direction in relation to the metal product;
  d) repeating steps a), b), and c); and
  e) collecting images of lines in a two-dimensional distribution of intensities and selecting a line direction of the metal product in which, if at least one wave of light intensities is detected, a local amplitude variation of the at least one wave defines a local strand flatness defect value, wherein the wave of light intensities detected results from a variation in orientation of a hollow or bump in each strand inducing a variation in an amplitude of intensities measured, which are compared to an evaluation of a length of each of the strands under its own intrinsic traction and having its own flatness value.

2. The method according to claim 1, wherein the illuminated portion extends at least over a width of the metal product and the strand direction selected is along a length of the metal product.

3. The method according to claim 1, wherein the metal product and devices providing illumination and image capture are in relative movement, either by travel of the metal product in the light line, or by movement of the devices providing illumination and image capture for the metal product which is motionless in the light line.

4. The method according to claim 1, which further comprises performing an illumination and image capture for a product cross-section, the product cross-section being located on a flat transverse zone.

5. The method according to claim 4, wherein the flat transverse zone is a succession of an upper roller generating lines known as a roller table, a conveyor belt or a fixed support table.

6. The method according to claim 1, which further comprises performing an illumination and image capture over a product cross-section, the product cross-section being observed on a deflecting roller.

7. The method according to claim 1, which further comprises performing an illumination and image capture for a product cross-section, the product cross-section being under tension between two deflecting rollers.

8. The method according to claim 1, which further comprises performing for a product cross-section, the product cross-section being at an input and/or output of a metallurgical processing section, the metal product being respectively mainly composed of a cold-rolled or hot-rolled metal.

9. The method according to claim 8, which further comprises selecting the metallurgical processing section from the group consisting of a rolling mill and a leveler.

10. The method according to claim 1, which further comprises subjecting the metal product to external longitudinal and/or transverse traction forces.

11. The method according to claim 1, which further comprises checking the flatness of the metal product for variable processing line thicknesses.

12. The method according to claim 1, wherein the illuminated portion is slender in shape over a width of the metal product and is generated by a light source disposed opposite the metal product which is traveling relative to the light source.

13. The method according to claim 12, which further comprises selecting the light source from the group consisting of at least one laser source and a strip light.

14. The method according to claim 1, which further comprises performing an illumination and image capture for a product cross-section, the product cross-section being under tension between two deflecting rollers, in a case when the metal product is a traveling metal strip.

15. The method according to claim 1, which further comprises checking the flatness of the metal product for variable processing line thicknesses between 0.1 mm and at least 150 mm.

16. A device for implementing a method for checking a flatness of a metal product, the device comprising:
at least one strip light positioned in a vicinity of a face of the metal product and illuminating a portion of the face of the metal product;
at least one linear camera to capture an image of the portion;
a transportation device for transporting the metal product along a direction of movement in a processing line providing for a relative movement of said at least one strip light and said at least one linear camera in the direction of movement in relation to the metal product;
a control module for controlling said strip light and said linear camera; and
a data processing unit for processing data delivered by said linear camera being images of the metal product for deducing flatness values of strands selected of the metal product, said data processing unit programmed to analyze a wave of light intensities resulting from a variation in orientation of a hollow or bump in each strand inducing a variation in an amplitude of intensities measured, which are compared to an evaluation of a length of each of the strands under its own intrinsic traction and having its own flatness value.

17. The device according to claim 16, further comprising a synchronization unit disposed between said control module and said transportation device.

18. The device according to claim 16, further comprising a module for measuring traction, wherein said data processing unit is connected to said module for measuring traction applied to the metal product, in addition to an intrinsic traction of the metal product.

19. The device according to claim 16, wherein said transportation device makes the metal product travel in front of an assembly formed by said strip light and said linear camera or vice-versa.

20. A production method, which comprises the steps of:
measuring a flatness of a metal product selected from the group consisting of strips and plates from a rolling mill or leveler operating regulator, the measuring step comprises the following sub-steps:
a) illuminating a portion of at least one face of the metal product under uniform intensity;
b) capturing an image of a light line of an illuminated portion of the metal product;
c) relatively moving the illuminated portion and the light line in a defined direction in relation to the metal product;
d) repeating steps a), b), and c);
e) collecting images of lines in a two-dimensional distribution of intensities and selecting a line direction of the metal product in which, if at least one wave of light intensities is detected, a local amplitude variation of the at least one wave defines a local strand flatness defect value;
forwarding the local strand flatness defect value as input data for the rolling mill or the leveler operating regulator; and
subsequently to the measuring of the flatness of the metal product emerging from the rolling mill or the leveler operating regulator, transmitting control instructions to evaluate and correct a measured flatness of the metal product emerging from the rolling mill or the leveler operating regulator.

* * * * *